(12) United States Patent
Gladwin et al.

(10) Patent No.: US 11,845,785 B2
(45) Date of Patent: *Dec. 19, 2023

(54) COMPOSITIONS AND METHODS FOR THE TREATMENT OF CARBOXYHEMOGLOBINEMIA

(71) Applicant: University of Pittsburgh—Of the Commonwealth System of Higher Education, Pittsburgh, PA (US)

(72) Inventors: Mark T. Gladwin, Pittsburgh, PA (US); Jesus Tejero Bravo, Pittsburgh, PA (US)

(73) Assignee: University of Pittsburgh—Of the CommonwealthSystem of Higher Education, Pittsburgh, PA (US)

( * ) Notice: Subject to any disclaimer, the term of this patent is extended or adjusted under 35 U.S.C. 154(b) by 178 days.

This patent is subject to a terminal disclaimer.

(21) Appl. No.: 16/951,529

(22) Filed: Nov. 18, 2020

(65) Prior Publication Data

US 2021/0070841 A1 Mar. 11, 2021

Related U.S. Application Data

(63) Continuation of application No. 16/557,168, filed on Aug. 30, 2019, now Pat. No. 10,851,153, which is a continuation of application No. 15/726,779, filed on Oct. 6, 2017, now Pat. No. 10,421,800, which is a continuation of application No. 14/776,363, filed as application No. PCT/US2014/023180 on Mar. 11, 2014, now abandoned.

(60) Provisional application No. 61/834,035, filed on Jun. 12, 2013, provisional application No. 61/799,155, filed on Mar. 15, 2013.

(51) Int. Cl.
| | | |
|---|---|---|
| *C07K 14/795* | (2006.01) | |
| *A61K 38/41* | (2006.01) | |
| *A61K 9/00* | (2006.01) | |
| *A61K 38/00* | (2006.01) | |

(52) U.S. Cl.
CPC .......... *C07K 14/795* (2013.01); *A61K 9/0019* (2013.01); *A61K 38/41* (2013.01); *A61K 38/00* (2013.01)

(58) Field of Classification Search
None
See application file for complete search history.

(56) References Cited

U.S. PATENT DOCUMENTS

| | | |
|---|---|---|
| 2010/0323029 A1 | 12/2010 | Gladwin et al. |
| 2011/0312914 A1 | 12/2011 | Kano et al. |
| 2016/0039910 A1 | 2/2016 | Gladwin et al. |
| 2018/0118810 A1 | 5/2018 | Gladwin et al. |
| 2019/0389937 A1 | 12/2019 | Gladwin et al. |

FOREIGN PATENT DOCUMENTS

| | | |
|---|---|---|
| CN | 102743456 | 10/2012 |

OTHER PUBLICATIONS

U.S. Appl. No. 14/776,363, Astudillo et al., Conformational Dynamics in Human Neuroglobin: Effect of His64, Val68, and Cys120 on Ligand Migration, *Biochem.*, 51:9984-9994, 2012.
U.S. Appl. No. 14/776,363, Bocahut et al., "Heme Orientation Modulates Histidine Dissociation and Ligand Binding Kinetics in the Hexacoordinated Human Neuroglobin," *J. Biol. Inorg. Chem.*, 18:111-122, 2013.
U.S. Appl. No. 14/776,363, Casado et al., "Human Neuroglobin Protein in Cerebrospinal Fluid," *Proteome Science*, 3:1-8, 2005.
U.S. Appl. No. 14/776,363, Gabba et al., "CO Rebinding Kinetics and Molecular Dynamics Simulations Highlight Dynamic Regulation of Internal Cavities in Human Cytoglobin," *PLoS ONE*, 8:e49770, 2013.
U.S. Appl. No. 15/726,779, Extended European Search Report for EP App. No. 18188514.6, mailed by the European Patent Office dated Feb. 5, 2019 (5 pages).
U.S. Appl. No. 14/776,363, Hampson et al., "Practice Recommendations in the Diagnosis, Management, and Prevention of Carbon Monoxide Poisoning," *Am J Respir Crit Care Med* 186(11):1095-1101, 2012.
U.S. Appl. No. 14/776,363, Kitagishi et al., "A Diatomic Molecule Receptor that Removes CO in a Living Organism," *Angew. Chem. Int. Ed.*, 49:1312-1315, 2010.
U.S. Appl. No. 14/776,363, Makino et al., "Crystal Structure of the Carbon Monoxide Complex of Human Cytoglobin," *Proteins*, 79:1143-1153, 2011.
U.S. Appl. No. 14/776,363, MD Nexus, Carboxyhemoglobinemia, Sep. 2, 2012.
U.S. Appl. No. 14/776,363, Nienhaus et al., "Structural Dynamics in the Active Site of Murine Neuroglobin and Its Effects on Ligand Binding," *J. Biol. Chem.*, 279: 22944-22952, 2004.
U.S. Appl. No. 14/776,363, Raub and Benignus, "Carbon Monoxide and the Nervous System," *Neurosci. Biobehav. Rev.*, 26:925-940, 2002.
U.S. Appl. No. 14/776,363, Sawai et al., "Structural Characterization of the Proximal and Distal Histidine Environment of Cytoglobin and Neuroglobin," *Biochem.*, 44:13257-13265, 2005.
U.S. Appl. No. 14/776,363, Tiso et al., "Human Neuroglobin Functions as a Redox-regulated Nitrite Reductase," *J Biol Chem* 286(20):18277-18289, 2011.

(Continued)

*Primary Examiner* — Julie Ha
*Assistant Examiner* — Tara L Martinez
(74) *Attorney, Agent, or Firm* — Klarquist Sparkman, LLP

(57) ABSTRACT

Described herein is a new antidote for the rapid elimination of carbon monoxide from hemoglobin, including brain, heart, and red cell hemoglobin. The disclosed therapy involves the use of modified human globins, particularly neuroglobins modified at residue 64 and cytoglobins modified at residue 81, which bind carbon monoxide with extremely high affinity. The monomeric mutant globins are infused into blood, where they rapidly and irreversibly sequester carbon monoxide, and thus limit toxic effects of carbon monoxide on cellular respiration and oxygen transport and utilization.

20 Claims, 9 Drawing Sheets
Specification includes a Sequence Listing.

(56) References Cited

OTHER PUBLICATIONS

U.S. Appl. No. 14/776,363, Weaver, "Carbon Monoxide Poisoning," *N Engl J Med* 360:1217-1225, 2009.
U.S. Appl. No. 15/726,779, Zhang et al., "Molecular dynamics simulation of carboxy and deoxy human cytoglobin in solution." *Journal of Inorganic Biochemistry* vol. 105, No. 7, pp. 949-956 (2011).
U.S. Appl. No. 14/776,363, Zhang et al., "Neuroglobin, a Novel Intracellular Hexa-Coordinated Globin, Functions as a Tumor Suppressor in Hepatocellular Carcinoma via Raf/MAPK/Erk," *Mol. Pharmacol.*, 83:1109-1119, 2013.

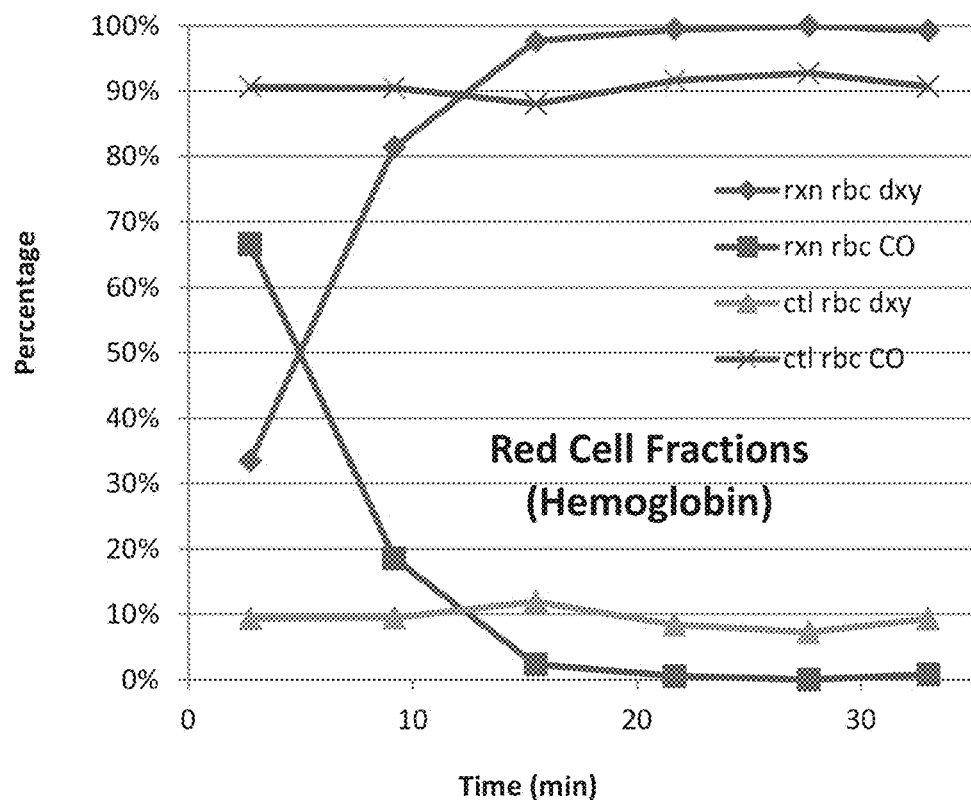
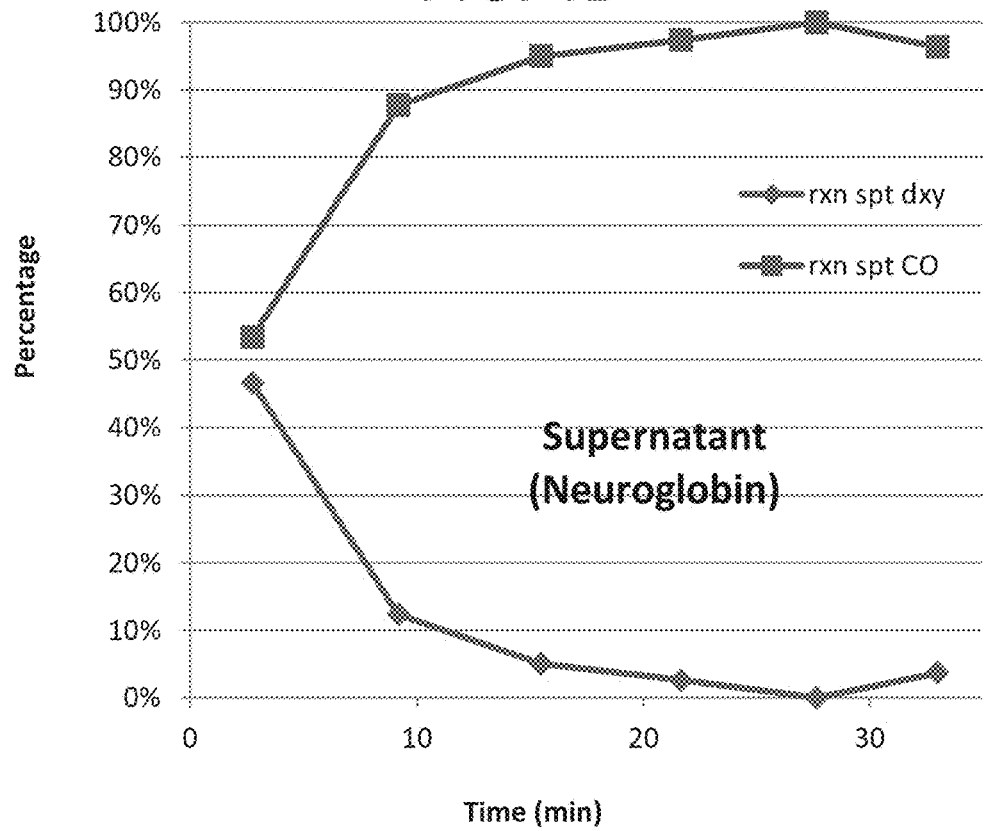

Time (min)

Concetration (μM)

SEQUENCE LISTING

```
<160> NUMBER OF SEQ ID NOS: 6

<210> SEQ ID NO 1
<211> LENGTH: 151
<212> TYPE: PRT
<213> ORGANISM: Homo sapiens

<400> SEQUENCE: 1

Met Glu Arg Pro Glu Pro Glu Leu Ile Arg Gln Ser Trp Arg Ala Val
1               5                   10                  15

Ser Arg Ser Pro Leu Glu His Gly Thr Val Leu Phe Ala Arg Leu Phe
            20                  25                  30

Ala Leu Glu Pro Asp Leu Leu Pro Leu Phe Gln Tyr Asn Cys Arg Gln
        35                  40                  45

Phe Ser Ser Pro Glu Asp Cys Leu Ser Ser Pro Glu Phe Leu Asp His
    50                  55                  60

Ile Arg Lys Val Met Leu Val Ile Asp Ala Ala Val Thr Asn Val Glu
65                  70                  75                  80

Asp Leu Ser Ser Leu Glu Glu Tyr Leu Ala Ser Leu Gly Arg Lys His
                85                  90                  95

Arg Ala Val Gly Val Lys Leu Ser Ser Phe Ser Thr Val Gly Glu Ser
            100                 105                 110

Leu Leu Tyr Met Leu Glu Lys Cys Leu Gly Pro Ala Phe Thr Pro Ala
        115                 120                 125

Thr Arg Ala Ala Trp Ser Gln Leu Tyr Gly Ala Val Val Gln Ala Met
    130                 135                 140

Ser Arg Gly Trp Asp Gly Glu
145                 150

<210> SEQ ID NO 2
<211> LENGTH: 151
```

```
<212> TYPE: PRT
<213> ORGANISM: Artificial Sequence
<220> FEATURE:
<223> OTHER INFORMATION: Recombinant polypeptide
<220> FEATURE:
<221> NAME/KEY: MISC_FEATURE
<222> LOCATION: (46)..(46)
<223> OTHER INFORMATION: Xaa = Cys or Gly
<220> FEATURE:
<221> NAME/KEY: MISC_FEATURE
<222> LOCATION: (55)..(55)
<223> OTHER INFORMATION: Xaa = Cys or Ser
<220> FEATURE:
<221> NAME/KEY: MISC_FEATURE
<222> LOCATION: (64)..(64)
<223> OTHER INFORMATION: Xaa = Gln, Leu, Ala, Trp
<220> FEATURE:
<221> NAME/KEY: MISC_FEATURE
<222> LOCATION: (120)..(120)
<223> OTHER INFORMATION: Xaa = Cys or Ser

<400> SEQUENCE: 2

Met Glu Arg Pro Glu Pro Glu Leu Ile Arg Gln Ser Trp Arg Ala Val
1               5                   10                  15

Ser Arg Ser Pro Leu Glu His Gly Thr Val Leu Phe Ala Arg Leu Phe
            20                  25                  30

Ala Leu Glu Pro Asp Leu Leu Pro Leu Phe Gln Tyr Asn Xaa Arg Gln
        35                  40                  45

Phe Ser Ser Pro Glu Asp Xaa Leu Ser Ser Pro Glu Phe Leu Asp Xaa
    50                  55                  60

Ile Arg Lys Val Met Leu Val Ile Asp Ala Ala Val Thr Asn Val Glu
65                  70                  75                  80

Asp Leu Ser Ser Leu Glu Glu Tyr Leu Ala Ser Leu Gly Arg Lys His
                85                  90                  95

Arg Ala Val Gly Val Lys Leu Ser Ser Phe Ser Thr Val Gly Glu Ser
            100                 105                 110

Leu Leu Tyr Met Leu Glu Lys Xaa Leu Gly Pro Ala Phe Thr Pro Ala
        115                 120                 125

Thr Arg Ala Ala Trp Ser Gln Leu Tyr Gly Ala Val Val Gln Ala Met
    130                 135                 140

Ser Arg Gly Trp Asp Gly Glu
145                 150

<210> SEQ ID NO 3
<211> LENGTH: 151
<212> TYPE: PRT
<213> ORGANISM: Artificial Sequence
<220> FEATURE:
<223> OTHER INFORMATION: Recombinant polypeptide

<400> SEQUENCE: 3

Met Glu Arg Pro Glu Pro Glu Leu Ile Arg Gln Ser Trp Arg Ala Val
1               5                   10                  15

Ser Arg Ser Pro Leu Glu His Gly Thr Val Leu Phe Ala Arg Leu Phe
            20                  25                  30

Ala Leu Glu Pro Asp Leu Leu Pro Leu Phe Gln Tyr Asn Gly Arg Gln
        35                  40                  45

Phe Ser Ser Pro Glu Asp Ser Leu Ser Ser Pro Glu Phe Leu Asp Gln
    50                  55                  60

Ile Arg Lys Val Met Leu Val Ile Asp Ala Ala Val Thr Asn Val Glu
65                  70                  75                  80

Asp Leu Ser Ser Leu Glu Glu Tyr Leu Ala Ser Leu Gly Arg Lys His
```

```
                    85                  90                  95

Arg Ala Val Gly Val Lys Leu Ser Ser Phe Ser Thr Val Gly Glu Ser
                100                 105                 110

Leu Leu Tyr Met Leu Glu Lys Ser Leu Gly Pro Ala Phe Thr Pro Ala
            115                 120                 125

Thr Arg Ala Ala Trp Ser Gln Leu Tyr Gly Ala Val Val Gln Ala Met
        130                 135                 140

Ser Arg Gly Trp Asp Gly Glu
145                 150

<210> SEQ ID NO 4
<211> LENGTH: 190
<212> TYPE: PRT
<213> ORGANISM: Homo sapiens

<400> SEQUENCE: 4

Met Glu Lys Val Pro Gly Glu Met Glu Ile Glu Arg Arg Glu Arg Ser
1               5                   10                  15

Glu Glu Leu Ser Glu Ala Glu Arg Lys Ala Val Gln Ala Met Trp Ala
            20                  25                  30

Arg Leu Tyr Ala Asn Cys Glu Asp Val Gly Val Ala Ile Leu Val Arg
        35                  40                  45

Phe Phe Val Asn Phe Pro Ser Ala Lys Gln Tyr Phe Ser Gln Phe Lys
    50                  55                  60

His Met Glu Asp Pro Leu Glu Met Glu Arg Ser Pro Gln Leu Arg Lys
65                  70                  75                  80

His Ala Cys Arg Val Met Gly Ala Leu Asn Thr Val Val Glu Asn Leu
                85                  90                  95

His Asp Pro Asp Lys Val Ser Ser Val Leu Ala Leu Val Gly Lys Ala
                100                 105                 110

His Ala Leu Lys His Lys Val Glu Pro Val Tyr Phe Lys Ile Leu Ser
            115                 120                 125

Gly Val Ile Leu Glu Val Val Ala Glu Glu Phe Ala Ser Asp Phe Pro
        130                 135                 140

Pro Glu Thr Gln Arg Ala Trp Ala Lys Leu Arg Gly Leu Ile Tyr Ser
145                 150                 155                 160

His Val Thr Ala Ala Tyr Lys Glu Val Gly Trp Val Gln Gln Val Pro
                165                 170                 175

Asn Ala Thr Thr Pro Pro Ala Thr Leu Pro Ser Ser Gly Pro
            180                 185                 190

<210> SEQ ID NO 5
<211> LENGTH: 190
<212> TYPE: PRT
<213> ORGANISM: Artificial Sequence
<220> FEATURE:
<223> OTHER INFORMATION: Recombinant polypeptide
<220> FEATURE:
<221> NAME/KEY: MISC_FEATURE
<222> LOCATION: (38)..(38)
<223> OTHER INFORMATION: Xaa = Cys or Ser
<220> FEATURE:
<221> NAME/KEY: MISC_FEATURE
<222> LOCATION: (81)..(81)
<223> OTHER INFORMATION: Xaa = Gln, Leu, Ala or Trp
<220> FEATURE:
<221> NAME/KEY: MISC_FEATURE
<222> LOCATION: (83)..(83)
<223> OTHER INFORMATION: Xaa = Cys or Ser

<400> SEQUENCE: 5
```

```
Met Glu Lys Val Pro Gly Glu Met Glu Ile Glu Arg Arg Glu Arg Ser
1               5                   10                  15

Glu Glu Leu Ser Glu Ala Glu Arg Lys Ala Val Gln Ala Met Trp Ala
            20                  25                  30

Arg Leu Tyr Ala Asn Xaa Glu Asp Val Gly Val Ala Ile Leu Val Arg
        35                  40                  45

Phe Phe Val Asn Phe Pro Ser Ala Lys Gln Tyr Phe Ser Gln Phe Lys
    50                  55                  60

His Met Glu Asp Pro Leu Glu Met Glu Arg Ser Pro Gln Leu Arg Lys
65                  70                  75                  80

Xaa Ala Xaa Arg Val Met Gly Ala Leu Asn Thr Val Val Glu Asn Leu
                85                  90                  95

His Asp Pro Asp Lys Val Ser Ser Val Leu Ala Leu Val Gly Lys Ala
            100                 105                 110

His Ala Leu Lys His Lys Val Glu Pro Val Tyr Phe Lys Ile Leu Ser
        115                 120                 125

Gly Val Ile Leu Glu Val Val Ala Glu Glu Phe Ala Ser Asp Phe Pro
    130                 135                 140

Pro Glu Thr Gln Arg Ala Trp Ala Lys Leu Arg Gly Leu Ile Tyr Ser
145                 150                 155                 160

His Val Thr Ala Ala Tyr Lys Glu Val Gly Trp Val Gln Gln Val Pro
            165                 170                 175

Asn Ala Thr Thr Pro Pro Ala Thr Leu Pro Ser Ser Gly Pro
                180                 185                 190

<210> SEQ ID NO 6
<211> LENGTH: 190
<212> TYPE: PRT
<213> ORGANISM: Artificial Sequence
<220> FEATURE:
<223> OTHER INFORMATION: Recombinant polypeptide

<400> SEQUENCE: 6

Met Glu Lys Val Pro Gly Glu Met Glu Ile Glu Arg Arg Glu Arg Ser
1               5                   10                  15

Glu Glu Leu Ser Glu Ala Glu Arg Lys Ala Val Gln Ala Met Trp Ala
            20                  25                  30

Arg Leu Tyr Ala Asn Ser Glu Asp Val Gly Val Ala Ile Leu Val Arg
        35                  40                  45

Phe Phe Val Asn Phe Pro Ser Ala Lys Gln Tyr Phe Ser Gln Phe Lys
    50                  55                  60

His Met Glu Asp Pro Leu Glu Met Glu Arg Ser Pro Gln Leu Arg Lys
65                  70                  75                  80

Gln Ala Ser Arg Val Met Gly Ala Leu Asn Thr Val Val Glu Asn Leu
                85                  90                  95

His Asp Pro Asp Lys Val Ser Ser Val Leu Ala Leu Val Gly Lys Ala
            100                 105                 110

His Ala Leu Lys His Lys Val Glu Pro Val Tyr Phe Lys Ile Leu Ser
        115                 120                 125

Gly Val Ile Leu Glu Val Val Ala Glu Glu Phe Ala Ser Asp Phe Pro
    130                 135                 140

Pro Glu Thr Gln Arg Ala Trp Ala Lys Leu Arg Gly Leu Ile Tyr Ser
145                 150                 155                 160
```

```
His Val Thr Ala Ala Tyr Lys Glu Val Gly Trp Val Gln Gln Val Pro
                165                 170                 175

Asn Ala Thr Thr Pro Pro Ala Thr Leu Pro Ser Ser Gly Pro
                180                 185                 190
```

COMPOSITIONS AND METHODS FOR THE TREATMENT OF CARBOXYHEMOGLOBINEMIA

CROSS REFERENCE TO RELATED APPLICATIONS

This application is a continuation of U.S. application Ser. No. 16/557,168, filed Aug. 30, 2019, issues as U.S. Pat. No. 10,851,153 on Dec. 1, 2020, which is a continuation of U.S. application Ser. No. 15/726,779, filed Oct. 6, 2017, issued as U.S. Pat. No. 10,421,800, on Sep. 24, 2019, which is a continuation of U.S. application Ser. No. 14/776,363, filed Sep. 14, 2015, now abandoned, which is the U.S. National Stage of International Application No. PCT/US2014/023180, filed Mar. 11, 2014, published in English under PCT Article 21(2), which claims the benefit of U.S. Provisional Application No. 61/834,035, filed Jun. 12, 2013, and U.S. Provisional Application No. 61/799,155, filed Mar. 15, 2013. The above-listed applications are herein incorporated by reference in their entirety.

ACKNOWLEDGMENT OF GOVERNMENT SUPPORT

This invention was made with government support under grant number HL103455 awarded by the National Institutes of Health. The government has certain rights in the invention.

FIELD

This disclosure concerns recombinant globin molecules, such as mutant forms of neuroglobin and cytoglobin, that bind carbon monoxide with very high affinity, and their use for the treatment of carboxyhemoglobinemia and carbon monoxide poisoning.

BACKGROUND

Inhalation exposure to carbon monoxide represents a major cause of environmental poisoning. Individuals can be exposed to carbon monoxide in the air under a variety of circumstances, such as house fires, use of generators or outdoor barbeque grills used inside the house, or during suicide attempts by running automobiles in closed spaces. Carbon monoxide binds to hemoglobin and to hemoproteins in cells, in particular, the enzymes of the respiratory transport chain. The accumulation of carbon monoxide bound to hemoglobin and other hemoproteins impairs oxygen delivery and oxygen utilization for oxidative phosphorylation. This ultimately results in severe hypoxic and ischemic injury to vital organs such as the brain and the heart. Individuals who accumulate greater than 15% carbon carboxyhemoglobin in their blood are at risk for brain injury and neurocognitive dysfunction. Individuals with higher levels of carboxyhemoglobin are at risk for death. Patients with very high carboxyhemoglobin levels typically suffer from irreversible brain injury and brain death.

Despite the availability of methods to rapidly diagnose carbon monoxide poisoning with standard arterial and venous blood gas analysis and co-oximetry, and despite an awareness of risk factors for carbon monoxide poisoning, there are no available antidotes for this toxic exposure. The current therapy is to give 100% oxygen by face mask, and when possible to expose patients to hyperbaric oxygen. The mechanism for hyperbaric oxygen therapy is the oxygen will increase the rate of release of the carbon monoxide from hemoglobin and from tissues and accelerate the natural clearance of carbon monoxide. However, this therapy has only a modest effect on carbon monoxide clearance rates and based on the complexity of hyperbaric oxygen facilities, this therapy is not available in the field.

SUMMARY

A need exists for an effective, rapid and readily available therapy to treat carboxyhemoglobinemia, also known as carbon monoxide poisoning. Provided by the present disclosure are modified globin molecules, such as recombinant forms of neuroglobin or cytoglobin, that bind carbon monoxide with very high affinity, thereby functioning as carbon monoxide scavengers. The data disclosed herein demonstrates that the modified globins can be used, for example, in methods of removing carbon monoxide from hemoglobin in blood or tissue, and in methods of treating carboxyhemoglobinemia.

Provided herein is a method of treating carboxyhemoglobinemia in a subject by selecting a subject with carboxyhemoglobinemia and administering to the subject a therapeutically effective amount of a recombinant globin molecule that binds carbon monoxide with high affinity. In some embodiments, the recombinant globin molecule is a recombinant human neuroglobin with a mutation at residue 64, such as a H64Q, H64L, H64A or H64W mutation, or a human recombinant cytoglobin with a mutation at residue 81, such as a H81Q, H81A, H81L or H81W mutation. In some examples, the recombinant globin molecules further comprise one or more cysteine amino acid substitutions to confer increased solubility. Increased solubility allows for the production of a high stock concentration of mutant globin for infusion of a dose sufficient for treatment of carboxyhemoglobinemia.

Also provided is a method of removing carbon monoxide from hemoglobin in blood or tissue by contacting the blood or tissue with a recombinant globin molecule that binds carbon monoxide with high affinity. In some embodiments, the recombinant globin molecule is a recombinant human neuroglobin with a mutation at residue 64, such as a H64Q, H64L, H64A or H64W mutation, or a human recombinant cytoglobin with a mutation at residue 81, such as a H81Q, H81A, H81L or H81W mutation. In some examples, the method of removing carbon monoxide from hemoglobin is an in vitro method. In other examples, the method is an in vivo method that includes administering the recombinant globin molecule to a subject in need of treatment.

Further provided are human recombinant neuroglobin proteins comprising a mutation at residue 64, and further comprising a C46G mutation, a C55S mutation and a C120S mutation. In some embodiments, the mutation at residue 64 is a H64Q, H64A, H64L or H64W mutation. Similarly, the present disclosure provides human recombinant cytoglobin proteins comprising a mutation at residue 81 and further comprising a C38S mutation and a C83S mutation. In some embodiments, the mutation at residue 81 is a H81Q, H81A, H81L or H81W mutation. Compositions comprising the recombinant neuroglobin or cytoglobin proteins and a pharmaceutically acceptable carrier are also provided by the present disclosure.

The foregoing and other objects, features, and advantages of the invention will become more apparent from the following detailed description, which proceeds with reference to the accompanying figures.

BRIEF DESCRIPTION OF THE DRAWINGS

FIGS. 1A-1B are graphs showing the reaction of carboxylated red blood cells (RBCs) with buffer or deoxy neuroglobin (deoxyNgb) H64Q. The experiments were performed at 21° C. in PBS buffer in anaerobic conditions. (FIG. 1A) Shown are deoxy or carboxylated species for the RBC fraction: deoxyHb during the RBC+Ngb experiment (diamonds); HbCO during the RBC+Ngb experiment (squares); HbCO during the RBC+buffer experiment (X); and deoxyHb during the RBC+buffer experiment (triangles). (FIG. 1B) Shown are deoxy or carboxylated species for the supernatant (neuroglobin) fraction: deoxyNgb during the RBC+Ngb experiment (diamonds); and NgbCO during the RBC+Ngb experiment (squares).

FIG. 7A shows absolute HbCO levels; FIG. 7B shows the relative change in HbCO level. Mice were exposed to 1500 ppm CO for 60-70 minutes, after which CO was stopped and concentrated H64Q Ngb (200 μl) was infused for 5 minutes. The infusion time was marked as t=0. Blood samples (about 10 μl) were drawn every 5-10 minutes, chemically reduced with dithionite and monitored for HbCO and NgbCO. Other Hb species in the blood (oxyHb/metHb/deoxyHb) are represented as deoxy Hb. Points represent the average and standard error of three or more experiments.

SEQUENCE LISTING

Figure 2:
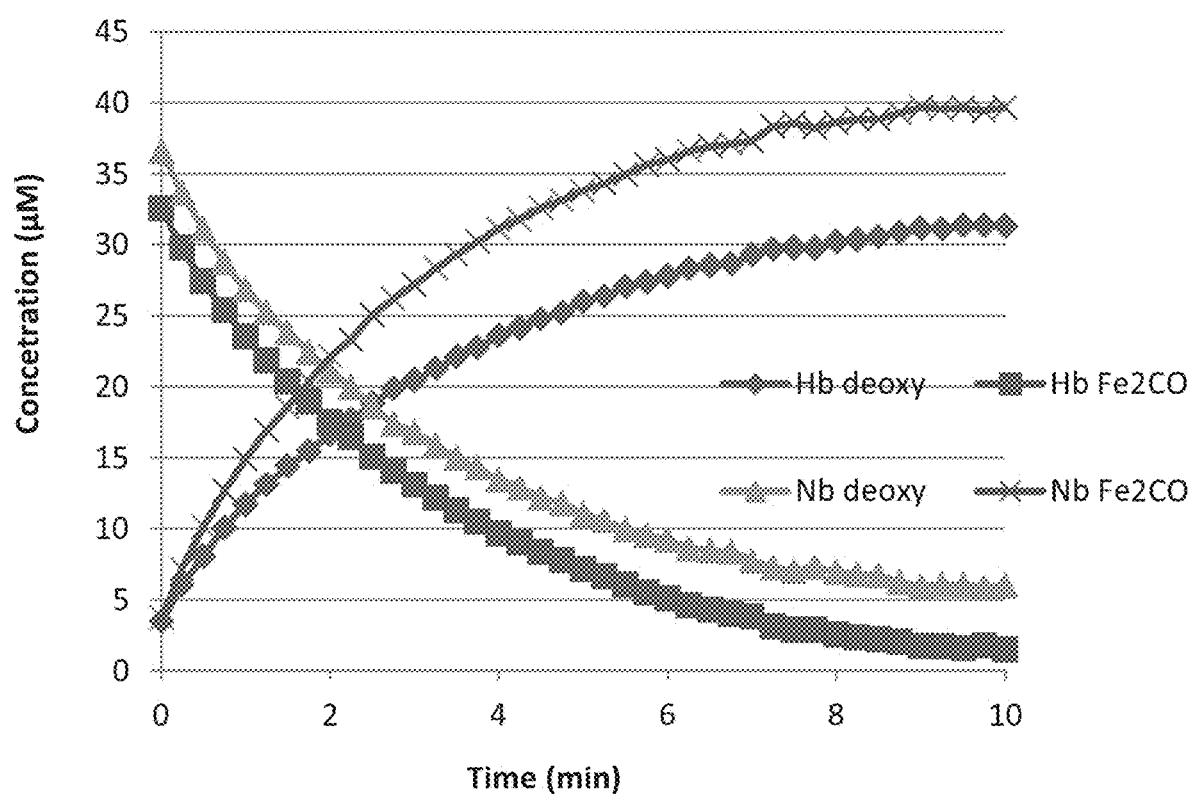
FIG. 2 is a graph showing the reaction of carboxylated red blood cells with deoxyNgb H64Q. The experiment was performed at 21° C. in PBS buffer in anaerobic conditions. Shown are deoxy or carboxylated species for the RBC fraction: deoxyHb (diamonds); HbCO (squares); deoxyNgb (triangles); and NgbCO (X).

The amino acid sequences listed in the accompanying sequence listing are shown using standard three letter code for amino acids, as defined in 37 C.F.R. 1.822. The Sequence Listing is submitted as an ASCII text file, created on Oct. 20, 2020, 10.1 KB, which is incorporated by reference herein. In the accompanying sequence listing:

SEQ ID NO: 1 is an amino acid sequence of human neuroglobin.

SEQ ID NO: 2 is the amino acid sequence of a recombinant human neuroglobin comprising one or more mutations.

SEQ ID NO: 3 is the amino acid sequence of a recombinant human neuroglobin comprising mutations at residues 46, 55, 64 and 120.

SEQ ID NO: 4 is an amino acid sequence of human cytoglobin.

SEQ ID NO: 5 is the amino acid sequence of a recombinant human cytoglobin comprising one or more mutations.

SEQ ID NO: 6 is the amino acid sequence of a recombinant human cytoglobin comprising mutations at residues 38, 81 and 83.

DETAILED DESCRIPTION

I. Abbreviations

Cgb cytoglobin
CO carbon monoxide
Hb hemoglobin
HbCO carboxyhemoglobin
Ngb neuroglobin
NgbCO carboxyneuroglobin
RBC red blood cell II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent (e.g. a recombinant polypeptide), by any effective route. Exemplary routes of administration include, but are not limited to, injection or infusion (such as subcutaneous, intramuscular, intradermal, intraperitoneal, intrathecal, intravenous, intracerebroventricular, intrastriatal, intracranial and into the spinal cord), oral, intraductal, sublingual, rectal, transdermal, intranasal, vaginal and inhalation routes.

Antidote: An agent that neutralizes or counteracts the effects of a poison.

Carbon monoxide (CO): A colorless, odorless and tasteless gas that is toxic to humans and animals when encountered at sufficiently high concentrations. CO is also produced during normal animal metabolism at low levels.

Carboxyhemoglobin (HbCO): A stable complex of carbon monoxide (CO) and hemoglobin (Hb) that forms in red blood cells when CO is inhaled or produced during normal metabolism.

Carboxyhemoglobinemia or carbon monoxide poisoning: A condition resulting from the presence of excessive amounts of carbon monoxide in the blood. Typically, exposure to CO of 100 parts per million (ppm) or greater is sufficient to cause carboxyhemoglobinemia. Symptoms of mild acute CO poisoning include lightheadedness, confusion, headaches, vertigo, and flu-like effects; larger exposures can lead to significant toxicity of the central nervous system and heart, and even death. Following acute poisoning, long-term sequelae often occur. Carbon monoxide can also have severe effects on the fetus of a pregnant woman. Chronic exposure to low levels of carbon monoxide can lead to depression, confusion, and memory loss. Carbon monoxide mainly causes adverse effects in humans by combining with hemoglobin to form carboxyhemoglobin (HbCO) in the blood. This prevents oxygen binding to hemoglobin, reducing the oxygen-carrying capacity of the blood, leading to hypoxia. Additionally, myoglobin and mitochondrial cytochrome oxidase are thought to be adversely affected. Carboxyhemoglobin can revert to hemoglobin, but the recovery takes time because the HbCO complex is fairly stable. Current methods of treatment for CO poisoning including administering 100% oxygen or providing hyperbaric oxygen therapy.

Contacting: Placement in direct physical association; includes both in solid and liquid form. When used in the context of an in vivo method, "contacting" also includes administering.

Cytoglobin: A globin molecule that is ubiquitously expressed in all tissues. Cytoglobin is a hexacoordinate hemoglobin that has been reported to facilitate diffusion of oxygen through tissues, reduce nitrite to nitric oxide, and play a cytoprotective role in hypoxic conditions and under oxidative stress. Human cytoglobin is 190 amino acids in length. An exemplary human cytoglobin amino acid sequence is set forth herein as SEQ ID NO: 4. The recombinant cytoglobin mutants disclosed herein, which exhibit very high affinity for CO, comprise a mutation at residue 81 (histidine to glutamine, alanine, tryptophan or leucine), and optionally comprise a cysteine to serine substitution at position 38 and/or a cysteine to serine substitution at position 83 (see SEQ ID NO: 5). In one non-limiting example, the cytoglobin mutant with high affinity for CO comprises the amino acid sequence of SEQ ID NO: 6.

Globin: A heme-containing protein involved in the binding and/or transport of oxygen. Globins include, for example, hemoglobin, myoglobin, neuroglobin and cytoglobin.

Hemoglobin (Hb): The iron-containing oxygen-transport metalloprotein in the red blood cells of the blood in vertebrates and other animals. In humans, the hemoglobin molecule is an assembly of four globular protein subunits. Each subunit is composed of a protein chain tightly associated with a non-protein heme group. Each protein chain arranges into a set of alpha-helix structural segments connected together in a globin fold arrangement, so called because this arrangement is the same folding motif used in other heme/globin proteins. This folding pattern contains a pocket which strongly binds the heme group.

Neuroglobin (Ngb): A member of the globin family of proteins. The physiological function of neuroglobin is currently unknown, but is thought to provide protection under hypoxic or ischemic conditions. Neuroglobin is expressed in the central and peripheral nervous system, cerebral spinal fluid, retina and endocrine tissues. Human neuroglobin is 151 amino acids in length. An exemplary human neuroglobin sequence is provided herein as SEQ ID NO: 1. The recombinant neuroglobin mutants disclosed herein, which exhibit very high affinity for CO, comprise a mutation at residue 64 (histidine to glutamine, alanine, tryptophan or leucine), and optionally comprise a cysteine to glycine substitution at residue 46, and/or a cysteine to serine substitution at position 55 and/or a cysteine to serine substitution at position 120 (see SEQ ID NO: 2). In one non-limiting example, the neuroglobin mutant with high affinity for CO comprises the amino acid sequence of SEQ ID NO: 3.

Peptide or Polypeptide: A polymer in which the monomers are amino acid residues which are joined together through amide bonds. When the amino acids are alpha-amino acids, either the L-optical isomer or the D-optical isomer can be used, the L-isomers being preferred. The terms "peptide," "polypeptide" or "protein" as used herein are intended to encompass any amino acid sequence and include modified sequences, including modified globin proteins. The terms "peptide" and "polypeptide" are specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histidine, is substituted for (or by) an electronegative residue, for example, glutamine or aspartic acid; or (d) a residue having a bulky side chain, for example, phenylalanine, is substituted for (or by) one not having a side chain, for example, glycine.

Pharmaceutically acceptable carriers: The pharmaceutically acceptable carriers of use are conventional. *Remington's Pharmaceutical Sciences*, by E. W. Martin, Mack Publishing Co., Easton, PA, 15th Edition, 1975, describes compositions and formulations suitable for pharmaceutical delivery of the compositions disclosed herein.

In general, the nature of the carrier will depend on the particular mode of administration being employed. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered by addition, substitution, or deletion of a portion of a natural nucleic acid molecule or protein.

Sequence identity/similarity: The identity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and C. elegans sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Subject: Living multi-cellular organisms, including vertebrate organisms, a category that includes both human and non-human mammals.

Therapeutically effective amount: A quantity of compound or composition, for instance, a recombinant globin molecule, sufficient to achieve a desired effect in a subject being treated. For instance, this can be the amount necessary to scavenge carbon monoxide in the blood or tissues, reduce the level of HbCO in the blood, and/or reduce one or more signs or symptoms associated with carbon monoxide poisoning.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Detailed Description

A need exists for an effective, rapid and readily available therapy to treat carboxyhemoglobinemia (including carbon monoxide poisoning). Disclosed herein is a new antidote that provides rapid elimination of carbon monoxide from the hemoglobin. The disclosed therapy involves the use of modified human globins, particularly neuroglobins modified at residue 64 (relative to SEQ ID NO: 1) and/or cytoglobins modified at residue 81 (relative to SEQ ID NO: 4) that bind carbon monoxide with extremely high affinity. The data disclosed herein demonstrate for the first time that mutant globins with high affinity for CO can very effectively remove CO from red blood cells; the CO is then cleared from the system through secretion in the urine. Thus, the mutant globin molecules described herein provide a surprisingly effective treatment for carboxyhemoglobinemia. The monomeric mutant globins are, for example, infused into blood in a subject, where they rapidly and irreversibly sequester carbon monoxide, and thus limit toxic effects of carbon monoxide on cellular respiration and oxygen transport and utilization.

A. Methods of treating carboxyhemoglobinemia or CO poisoning

Provided herein is a method of treating carboxyhemoglobinemia in a subject by selecting a subject with carboxyhemoglobinemia and administering to the subject a therapeutically effective amount of a recombinant globin molecule that binds carbon monoxide with high affinity. In some embodiments, the recombinant globin molecule is a recombinant human neuroglobin with a mutation (an amino acid substitution) at residue 64, such as a H64Q, H64L, H64A or H64W mutation, or a human recombinant cytoglobin with a mutation at residue 81, such as a H81Q, H81A, H81L or H81W mutation. Throughout this disclosure, the amino acid positions of human recombinant neuroglobin and human recombinant cytoglobin are based on the wild-type human neuroglobin and wild-type human cytoglobin sequences set forth herein as SEQ ID NO: 1 and SEQ ID NO: 4, respectively.

The recombinant globin molecules can further include one or more cysteine amino acid substitutions to confer increased solubility. Increased solubility allows for the production of a high stock concentration of mutant globin for infusion of a dose sufficient for treatment of carboxyhemoglobinemia. In some embodiments, human recombinant neuroglobin further comprises a C46G mutation, a C55S mutation, a C120S mutation, or any combination thereof. In particular examples, the recombinant neuroglobin comprises all three cysteine substitutions. In one non-limiting example, the human recombinant neuroglobin comprises the amino acid sequence of SEQ ID NO: 3. In some embodiments, human recombinant cytoglobin further comprises a C38S mutation, or a C83S mutation, or both a C38S and a C83S mutation. In one non-limiting example, the human recombinant cytoglobin comprises the amino acid sequence of SEQ ID NO: 6.

In alternative embodiments, the human recombinant neuroglobin comprising a mutation at residue 64, and optionally one, two or three cysteine substitutions (i.e., one, two or all three of the C46G, C55S and C120S mutations) can include one or more conservative or non-conservative amino acid substitutions at other residues. Similarly, the human recombinant cytoglobin comprising a mutation at residue 81, and optionally one or both of the cysteine substitutions (i.e. one or both of the C38S and C83S mutations) can include one or more conservative or non-conservative amino acid substitutions at other residues. In some examples, the human recombinant neuroglobin or cytoglobin comprises one, two, three, four, five, six, seven, eight, nine or ten conservative amino acid substitutions, or one, two, three, four, five, six, seven, eight, nine or ten non-conservative amino acid substitutions, or any combination of conservative and non-conservative substitutions, as long as the recombinant globin retains the capacity to bind carbon monoxide with high affinity. In some examples, the recombinant human neuroglobin or cytoglobin includes a deletion, such as a deletion of one, two, three, four, five, six, seven, eight, nine, ten or more amino acids, while still maintaining the capacity to bind carbon monoxide with high affinity.

In some examples, the human recombinant neuroglobin comprising a mutation at residue 64, and optionally one, two or three cysteine substitutions (i.e., one, two or all three of the C46G, C55S and C120S mutations), is at least 85%, at least 90%, at least 95%, at least 96%, at least 97%, at least 98% or at least 99% identical to SEQ ID NO: 1 or SEQ ID NO: 3.

In some examples, the human recombinant cytoglobin comprising a mutation at residue 81, and optionally one or both of the cysteine substitutions (i.e. one or both of the C38S and C83S mutations) is at least 85%, at least 90%, at least 95%, at least 96%, at least 97%, at least 98% or at least 99% identical to SEQ ID NO: 4 or SEQ ID NO: 6.

In some embodiments, the subject has at least 3%, at least 5%, at least 10%, at least 15% or at least 20% carboxyhemoglobin (HbCO) in their blood.

In some embodiments, the recombinant globin molecule is administered intravenously, such as by intravenous infusion.

An appropriate dose of recombinant neuroglobin or cytoglobin can be determined by a medical practitioner. In some embodiments, the dose is the amount of recombinant globin required to decrease HbCO at least 1%, at least 2%, at least 3%, at least 4%, at least 5%, at least 10%, at least 15%, at least 20%, at least 25%, at least 30%, at least 40%, at least 50%, at least 60%, at least 70%, at least 80% or at least 90%. Generally, a dose of about 136 grams of neuroglobin or about 184 grams of cytoglobin is sufficient to achieve a 20% reduction in HbCO.

Thus, in some embodiments, the therapeutically effective dose of human recombinant neuroglobin is about 25 to about 1000 grams, about 50 to about 500 grams, about 50 to about 200 grams, or about 60 to about 140 grams. In particular examples, the therapeutically effective dose of human recombinant neuroglobin is about 50, about 75, about 100, about 150, about 200, about 250, about 300, about 350, about 400, about 450 or about 500 grams. In some embodiments, the therapeutically effective dose of human recombinant cytoglobin is about 25 to about 1000 grams, or about 50 to about 800 grams. In particular examples, the therapeutically effective does of human recombinant cytoglobin is about 50, about 75, about 100, about 150, about 200, about 250, about 300, about 350, about 400, about 450, about 500, about 550, about 600, about 650, about 700, about 750 or about 800 grams.

In some embodiments, the neuroglobin or cytoglobin concentration administered to a subject is about 70 to about 200 grams per liter, which equates to approximately 35-200 grams for a 500 milliliter or 1 liter treatment.

The modified globin with high affinity for carbon monoxide can be administered to a subject in a single dose, or in multiple doses as needed, to reduce HbCO to a non-toxic level.

In some embodiments, the dose administered to the subject is the amount of recombinant globin required to decrease HbCO by at least 1%, at least 2%, at least 3%, at least 4%, at least 5%, at least 10%, at least 15%, at least 20%, at least 25%, at least 30%, at least 40%, at least 50%, at least 60%, at least 70%, at least 80% or at least 90% (compared to the level of HbCO before treatment) in blood and/or tissue of the subject.

B. Methods of removing carbon monoxide from hemoglobin

Also provided herein is a method of removing carbon monoxide from hemoglobin in blood or tissue by contacting the blood or tissue with a recombinant globin molecule that binds carbon monoxide with high affinity. In the context of the present disclosure, "removing" does not require complete elimination of carbon monoxide from the blood or tissue, but rather means removal of CO from hemoglobin molecules in blood or tissue such that the overall level of HbCO is reduced in the blood or tissue of a sample or subject. For example, the HbCO can be reduced by at least 1%, at least 2%, at least 3%, at least 4%, at least 5%, at least 10%, at least 15%, at least 20% or at least 25% (compared to the level of HbCO before treatment) in the blood and/or tissue.

In some embodiments of the method, the recombinant globin molecule is a recombinant human neuroglobin with a mutation at residue 64, such as a H64Q, H64L, H64A or H64W mutation, or a human recombinant cytoglobin with a mutation at residue 81, such as a H81Q, H81A, H81L or H81W mutation.

The recombinant globin molecules can further include one or more cysteine amino acid substitutions to confer increased solubility. Increased solubility allows for the production of a high stock concentration of mutant globin for infusion of a dose sufficient for effective removal of CO from the blood. In some embodiments, human recombinant neuroglobin further comprises a C46G mutation, a C55S mutation, a C120S mutation, or any combination thereof. In particular examples, the recombinant neuroglobin comprises all three cysteine substitutions. In one non-limiting example, the human recombinant neuroglobin comprises the amino acid sequence of SEQ ID NO: 3. In some embodiments, human recombinant cytoglobin further comprises a C38S mutation, or a C83S mutation, or both a C38S and a C83S mutation. In one non-limiting example, the human recombinant cytoglobin comprises the amino acid sequence of SEQ ID NO: 6.

In alternative embodiments, the human recombinant neuroglobin comprising a mutation at residue 64, and optionally one, two or three cysteine substitutions (i.e., one, two or all three of the C46G, C55S and C120S mutations) can include one or more conservative or non-conservative amino acid substitutions at other residues. Similarly, the human recombinant cytoglobin comprising a mutation at residue 81, and optionally one or both of the cysteine substitutions (i.e. one or both of the C38S and C83S mutations) can include one or more conservative or non-conservative amino acid substitutions at other residues. In some examples, the human recombinant neuroglobin or cytoglobin comprises one, two, three, four, five, six, seven, eight, nine or ten conservative amino acid substitutions, or one, two, three, four, five, six, seven, eight, nine or ten non-conservative amino acid substitutions, or any combination of conservative and non-conservative substitutions, as long as the recombinant globin retains the capacity to bind carbon monoxide with high affinity. In some examples, the recombinant human neuroglobin or cytoglobin includes a deletion, such as a deletion of one, two, three, four, five, six, seven, eight, nine, ten or more amino acids, while still maintaining the capacity to bind carbon monoxide with high affinity.

In some examples, the human recombinant neuroglobin comprising a mutation at residue 64, and optionally one, two or three cysteine substitutions (i.e., one, two or all three of the C46G, C55S and C120S mutations), is at least 85%, at least 90%, at least 95%, at least 96%, at least 97%, at least 98% or at least 99% identical to SEQ ID NO: 1 or SEQ ID NO: 3.

In some examples, the human recombinant cytoglobin comprising a mutation at residue 81, and optionally one or both of the cysteine substitutions (i.e. one or both of the C38S and C83S mutations) is at least 85%, at least 90%, at least 95%, at least 96%, at least 97%, at least 98% or at least 99% identical to SEQ ID NO: 4 or SEQ ID NO: 6.

In some examples, the method of removing carbon monoxide from hemoglobin is an in vitro method. For example, the method can include contacting a blood or tissue sample with the recombinant globin molecule. In some examples, a sufficient amount of recombinant globin is contacted with the blood or tissue sample such that HbCO is reduced in the sample by at least 1%, at least 2%, at least 3%, at least 5%, at least 10%, at least 15%, at least 20%, at least 25%, at least 30%, at least 40%, at least 50%, at least 60%, at least 70%, at least 80% or at least 90%.

In other examples, the method is an in vivo method that includes administering the recombinant globin molecule to a subject in need of treatment. In some cases, the subject (prior to administration) has at least 3%, at least 5%, at least 10%, at least 15% or at least 20% HbCO in their blood. The recombinant globin molecule can be administered using any suitable route of administration, such as intravenous administration, for example intravenous infusion.

Appropriate, therapeutically effective doses of recombinant neuroglobin and cytoglobin are discussed above in section A. In some examples, the therapeutically effective dose of human recombinant neuroglobin is about 25 to about 1000 grams, or about 50 to about 500 grams. In some examples, the therapeutically effective dose of human recombinant cytoglobin is about 25 to about 1000 grams, or about 50 to about 800 grams. The modified globin with high affinity for carbon monoxide can be administered to a subject in a single dose, or in multiple doses as needed, to reduce HbCO to a non-toxic level.

In some embodiments of the in vivo method, the dose administered to the subject is the amount of recombinant globin required to decrease HbCO at least 1%, at least 2%, at least 3%, at least 5%, at least 10%, at least 15%, at least 20%, at least 25%, at least 30%, at least 40%, at least 50%, at least 60%, at least 70%, at least 80% or at least 90% in blood and/or tissue of the subject.

C. Recombinant neuroglobin and cytoglobin mutants

Provided herein are human recombinant neuroglobin proteins comprising a mutation at residue 64 (relative to SEQ ID NO: 1), and further comprising a C46G mutation, a C55S mutation and a C120S mutation. In some embodiments, the mutation at residue 64 is a H64Q, H64A, H64L or H64W mutation. Similarly, the present disclosure provides human recombinant cytoglobin proteins comprising a mutation at residue 81 (relative to SEQ ID NO: 4) and further comprising a C38S mutation and a C83S mutation. In some embodiments, the mutation at residue 81 is a H81Q, H81A, H81L or H81W mutation. Further provided are compositions comprising the recombinant neuroglobin or cytoglobin proteins disclosed herein and a pharmaceutically acceptable carrier.

Data disclosed herein (see Example 2) demonstrates for the first time that neuroglobin molecules comprising the H64L or H64Q mutation have auto-oxidation rates 23-fold slower than the wild type protein. A lower auto-oxidation rate is a desirable property because it reduces side reactions that are detrimental to the ability of the mutant globin to bind CO and deliver oxygen to tissues.

Wild-type human neuroglobin and wild-type human cytoglobin amino acid sequences are shown below, along with exemplary recombinant neuroglobin and cytoglobin mutants provided by the present disclosure.

Human neuroglobin
(SEQ ID NO: 1; GenBank ™ Accession No. NP_067080.1)
MERPEPELIRQSWRAVSRSPLEHGTVLFARLFALEPDLLPLFQYNCRQFS

SPEDCLSSPEFLDHIRKVMLVIDAAVTNVEDLSSLEEYLASLGRKHRAVG

VKLSSFSTVGESLLYMLEKCLGPAFTPATRAAWSQLYGAVVQAMSRGWDG

E

Recombinant neuroglobin with high affinity for CO
(SEQ ID NO: 2)
MERPEPELIRQSWRAVSRSPLEHGTVLFARLFALEPDLLPLFQYNX$_1$RQF

SSPEDX$_2$LSSPEFLDX$_3$IRKVMLVIDAAVTNVEDLSSLEEYLASLGRKHR

AVGVKLSSFSTVGESLLYMLEKX$_2$LGPAFTPATRAAWSQLYGAVVQAMSR

GWDGE

X$_1$ = C or G

X$_2$ = C or S

X$_3$ = Q, L, A or W

Recombinant neuroglobin with four amino acid substitutions
(SEQ ID NO: 3)
MERPEPELIRQSWRAVSRSPLEHGTVLFARLFALEPDLLPLFQYNGRQFS

SPEDSLSSPEFLDQIRKVMLVIDAAVTNVEDLSSLEEYLASLGRKHRAVG

VKLSSFSTVGESLLYMLEKSLGPAFTPATRAAWSQLYGAVVQAMSRGWDG

E

Human cytoglobin
(SEQ ID NO: 4; GenBank ™ Accession No. NP_599030)
MEKVPGEMEIERRERSEELSEAERKAVQAMWARLYANCEDVGVAILVRFF

VNFPSAKQYFSQFKHMEDPLEMERSPQLRKHACRVMGALNTVVENLHDPD

KVSSVLALVGKAHALKHKVEPVYFKILSGVILEVVAEEFASDFPPETQRA

WAKLRGLIYSHVTAAYKEVGWVQQVPNATTPPATLPSSGP

```
Recombinant cytoglobin with high CO affinity
                                         (SEQ ID NO: 5)
MEKVPGEMEIERRERSEELSEAERKAVQAMWARLYANX₁EDVGVAILVRF

FVNFPSAKQYFSQFKHMEDPLEMERSPQLRKX₂AX₁RVMGALNTVVENLH

DPDKVSSVLALVGKAHALKHKVEPVYFKILSGVILEVVAEEFASDFPPET

QRAWAKLRGLIYSHVTAAYKEVGWVQQVPNATTPPATLPSSGP

X₁ = C or S

X₂ = Q, L, A or W

Recombinant cytoglobin with three amino acid
substitutions
                                         (SEQ ID NO: 6)
MEKVPGEMEIERRERSEELSEAERKAVQAMWARLYANSEDVGVAILVRFF

VNFPSAKQYFSQFKHMEDPLEMERSPQLRKQASRVMGALNTVVENLHDPD

KVSSVLALVGKAHALKHKVEPVYFKILSGVILEVVAEEFASDFPPETQRA

WAKLRGLIYSHVTAAYKEVGWVQQVPNATTPPATLPSSGP
```

The human recombinant neuroglobin and cytoglobin proteins provided herein can comprises one of the sequences shown above (and set forth herein as SEQ ID NOs: 2, 3, 5 and 6), or the recombinant globins can further include one or more conservative or non-conservative amino acid substitutions. For example, the human recombinant neuroglobin with mutations at residues 46, 55, 64 and 120 can include one or more conservative or non-conservative amino acid substitutions at other residues. Similarly, the human recombinant cytoglobin comprising mutations at residues 38, 81 and 83 can include one or more conservative or non-conservative amino acid substitutions at other residues. In some examples, the human recombinant neuroglobin or cytoglobin comprises one, two, three, four, five, six, seven, eight, nine or ten conservative amino acid substitutions, or one, two, three, four, five, six, seven, eight, nine or ten non-conservative amino acid substitutions, or any combination of conservative and non-conservative substitutions, as long as the recombinant globin retains the capacity to bind carbon monoxide with high affinity. In some examples, the recombinant human neuroglobin or cytoglobin includes a deletion, such as a deletion of one, two, three, four, five, six, seven, eight, nine, ten or more amino acids, while still maintaining the capacity to bind carbon monoxide with high affinity.

In some examples, the human recombinant neuroglobin is at least 85%, at least 90%, at least 95%, at least 96%, at least 97%, at least 98% or at least 99% identical to SEQ ID NO: 2 or SEQ ID NO: 3 and retains the modification at residue 64 (H64Q, H64A, H64W or H64L) and the C46G, C55S and C120S mutations.

In some examples, the human recombinant cytoglobin is at least 85%, at least 90%, at least 95%, at least 96%, at least 97%, at least 98% or at least 99% identical to SEQ ID NO: 6 and retains the modification at residue 81 (H81Q, H81A, H81W or H81L) and the C38S and C83S mutations.

Compositions comprising any of the recombinant globin molecules disclosed herein and a pharmaceutically acceptable carrier, are also provided by the present disclosure.

The following examples are provided to illustrate certain particular features and/or embodiments. These examples should not be construed to limit the disclosure to the particular features or embodiments described.

EXAMPLES

Example 1

Scavenging of Carbon Monoxide (CO) from Hemoglobin by the Neuroglobin H64Q Mutant This example demonstrates that H64Q mutant neuroglobin rapidly removes CO from carboxylated hemoglobin located inside red blood cells.

Background

Neuroglobin (Ngb) is a heme protein, recently discovered in mammals and other species (Burmester et al., *Nature* 407(6803):520-523, 2000). Ngb is very similar in sequence and structure to myoglobin and hemoglobin, but unlike these proteins it contains a six-coordinated heme with two histidine groups binding to the heme, whereas myoglobin and hemoglobin are five-coordinated and only have one histidine permanently bound to the heme. The function of this heme protein is unknown. The reaction of the iron atom from a heme group can be depicted as follows:

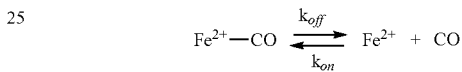

where $k_{on}$ and $k_{off}$ are the rates of CO binding and dissociation, respectively. Ngb shows high affinity for ligands such as oxygen or carbon monoxide, and this affinity is even higher when the distal histidine (His64) is replaced by other side chains (Table 1).

TABLE 1

Binding and dissociation constants for neuroglobin and hemoglobin

| | $k_{on}$ ($M^{-1}s^{-1}$) | $k_{off}$ ($s^{-1}$) |
|---|---|---|
| Human Ngb wt | 65 × 10⁶ | 0.014 |
| Mouse Ngb wt | 72 × 10⁶ | 0.013 |
| Mouse Ngb H64L | 200 × 10⁶ | ND (too slow) |
| Human Hb (α subunit, R-state) | 6 × 10⁶ | 0.012 |
| Human Hb (α subunit, T-state) | 0.12 × 10⁶ | 0.21 |
| Human Hb (β subunit, R-state) | 7.4 × 10⁶ | 0.007 |
| Human Hb (β subunit, T-state) | 0.05 × 10⁶ | 0.19 |

Values determined at 25° C.
Neuroglobin data from Dewilde et al., *J Biol Chem* 276(42): 38949-38955, 1998.
Hemoglobin data from Unzai et al., *J Biol Chem* 273(36): 23150-23159, 1998.

Based on previous characterization (Tiso et al., *J Biol Chem* 286(20):18277-18289, 2011) and subsequent studies, it is believed that the CO binding properties of the H64Q and H64L mutants are very similar, therefore the reported values for H64L are a reasonable estimate for H64Q. The data in Table 1 indicates that in the presence of an adequate scavenger, the CO dissociation from hemoglobin will lead to a half-life of the HbCO complex of approximately 3.5 seconds (T-state) or 70 seconds (R-state) at 25° C. Higher rates may lead to even shorter times at 37° C. These short times offer an opportunity for a therapeutic approach. However, in the absence of CO scavengers, the dissociated CO will eventually bind again to hemoglobin, leading to a persistence of HbCO much longer than suggested by the dissociation rates.

The binding and dissociation rates for neuroglobin (Table 1) indicate a much higher affinity towards CO than that of hemoglobin. Therefore, it was hypothesized that neuroglobin would be a suitable scavenger of CO from HbCO or other carboxylated compounds. The results described below confirm this hypothesis.

Materials and Methods

Reagents

Blood was used fresh or up to 2 weeks after collection from healthy volunteers. Red blood cells (RBCs) and hemoglobin were prepared as described previously (Huang et al., *J Clin Invest* 115(8):2099-2107, 2005). All chemicals were purchased from Sigma (St. Louis, MO) unless noted otherwise. Visible absorbance spectra and kinetic data were collected on Cary 50 and HP8453 UV-visible spectrophotometers (Agilent Technologies, Palo Alto, CA) and with an SX20 Stopped-Flow Spectrometer (Applied Photophysics Limited, Leatherhead, UK). All experiments were performed in phosphate buffered saline (Sigma). Carbon monoxide (CO)-saturated buffer was prepared by bubbling 20 mL of PBS with CO gas for at least 15 minutes. Stock sodium dithionite solution was prepared by adding PBS degassed by Argon flow-through to a degassed vial of dry sodium dithionite.

Expression and Purification of Recombinant Neuroglobin

Recombinant neuroglobin (Ngb) H64Q protein was purified from *E. coli* cultures from a modified method based on previous work (Tiso et al., *J Biol Chem* 286(20):18277-18289, 2011). SoluBL21 *E. coli* cells (Genlantis) containing the pET28-NgbH64Q plasmid were grown in TB broth supplemented with 30 µg/ml Kanamycin. Expression was induced at $OD_{600}$ nm=0.8 by adding 1 mM isopropyl-1-thio-β-D-galactopyranoside and carried out for 24 hours at 37° C. δ-aminolevulinic acid (0.4 mM) was added at induction to enhance the production of the heme cofactor. Cells were harvested and resuspended in lysis buffer (50 mM MOPS, pH 7.0, 1 mM EDTA, 1 mg/ml lysozyme, 1 mM PMSF, 0.5 mM DTT) and lysed by sonication. Supernatant was loaded into a DEAE-sepharose column equilibrated with buffer A (50 mM MOPS pH 7.0, 10 mM NaCl). The samples were washed with 3 column volumes of buffer A and eluted by a linear gradient to 100% buffer B (50 mM MOPS pH 7.0, 100 mM NaCl). Ngb fractions were pooled and concentrated. For further purification, the concentrated samples were run in a gel filtration column (Sephacryl S-200 HR, GE Healthcare). Purity was assessed by SDS-PAGE and UV-Vis spectroscopy.

Kinetics of carboxylated Hb mixed with neuroglobin

Carboxylated Hb (HbCO) was prepared by adding an excess of sodium dithionite to thawed Hb and mixing with CO-saturated buffer at a ratio of at least 4:1. Excess CO was removed by passing through a desalting column inside a glove box. For anaerobic experiments, an excess of sodium dithionite was then added to the HbCO. Thawed Ngb-H64Q was mixed with an excess of potassium ferricyanide and passed through a desalting column to obtain the oxidized form. In some instances, Ngb-H64Q was already stored in the oxidized form at −80° C. Deoxygenated Ngb-H64Q was obtained by adding an excess of sodium dithionite to the oxidized form. For aerobic experiments, the oxygenated form was obtained by passing the deoxygenated form through a desalting column under aerobic conditions immediately before mixing with HbCO.

For kinetics measured with the Cary 50 or the HP8453 spectrophotometer, HbCO inside a cuvette of 1 cm path length was placed in the cell holder and brought to either 25° C. or 37° C. The deoxygenated or oxygenated Ngb-H64Q was quickly equilibrated to the same temperature using a water bath next to the spectrophotometer. Reaction was initiated by injecting Ngb-H64Q into the HbCO solution for a final concentration of 40 µM of both proteins. Collection of absorbance was initiated with a delay of 1 to 10 seconds and continued for up to 20 minutes as the mixture was continuously stirred. A final concentration of 1-5 mM of sodium dithionite was present in anaerobic reactions. For kinetics measured with the SX20 Stopped-Flow Spectrometer, the sample lines of the instrument were first washed with pure PBS for aerobic experiments and with PBS containing 5 mM sodium dithionite for anaerobic experiments. The sample lines and syringes of the apparatus were equilibrated to either 25° C. or 37° C. HbCO and Ngb-H6Q were then loaded into 2.5 ml syringes of the apparatus that contained 5 mM sodium dithionite for anaerobic experiments. HbCO and Ngb-H64Q were mixed 1:1 with a dead time of less than 2 msec for a final concentration of 25-30 µM of both proteins. Absorbance of the reaction mixture was followed for no more than 200 seconds.

Kinetics of carboxylated RBCs mixed with neuroglobin

Red cells were obtained by washing 50-100 µL, of blood with PBS 5 to 7 times by centrifugation at 1000×g for 5-10 minutes. The washed red cells were diluted in 1 to 2 ml of PBS and deoxygenated while on ice and slow stirring by a passing flow of argon gas for up to 1 hour. For anaerobic experiments, argon was passed briefly and an excess of sodium dithionite to Hb was added to the red cells. Carboxylated red cell-encapsulated Hb was obtained by diluting the deoxygenated red cell solution with a ratio of at least 4:1. Excess CO was removed by washing the red cells 2 times with degassed PBS (containing 5-10 mM dithionite for anaerobic experiments) by centrifugation for 5 minutes at 1000×g in degassed and septum-capped 15 mL centrifuge tubes. After washing, the red cells were resuspended to a final concentration of 100-200 µM, with an excess of sodium dithionite for anaerobic experiments.

Oxygenated or deoxygenated Ngb-H64Q was prepared following the same procedure as that described for the experiments with pure Hb. In some experiments, after initiating the reaction, red cells were separated from Ngb-H64Q to measure absorbance spectra. In this case, the reaction temperature was regulated with an ISOTEMP™ stirring hotplate and water bath combination (Fisher Scientific). Red cell-encapsulated HbCO and oxygenated or deoxygenated Ngb-H64Q were equilibrated to 25° C. or 37° C. in separate glass vials. Reaction was initiated by injecting Ngb-H64Q into the red cell solution for a final concentration of 40 µM of both proteins. An equivalent volume of PBS (with or without dithionite) was injected into a control sample of carboxylated red cells. Periodically, 0.5 ml of the reaction and the control sample were taken and centrifuged for 30-60 seconds at 5000×g in 1.5 mL microcentrifuge tubes. The supernatant containing Ngb-H64Q was removed (5 mM sodium dithionite was added in aerobic experiments to prevent auto-oxidation of the protein) and stored on ice.

A solution of 0.5% NP40 in PBS (always containing 5 mM sodium dithionite for anaerobic experiments and sometimes for aerobic) was added to the red cell pellet to lyse the cells. Hb absorbance in the lysed red cell solution was measured with the Cary 50 spectrophotometer in a 1 cm path length cuvette. This cycle was repeated every 1.5-5 minutes for a total of six times, giving six absorbance measurements of the Hb. The control and reaction samples were continuously stirred. The time when absorbance of hemoglobin was measured in the reaction was assumed to be the time elapsed after injection of Ngb-H64Q to 15 or 30 seconds after the start of centrifugation (for 30 or 60 second centrifugation durations, respectively). After the last ($6^{th}$) time point was measured, absorbance of the stored supernatant samples of the reaction and control mixtures was recorded as well. In some experiments, the red cells were not separated from Ngb-H64Q; instead, absorbance of the whole mixture was recorded with the Integrating Sphere attachment of a Cary 100 spectrophotometer. This setup collects light scattered by the red cells, thereby providing absorbance spectra sufficiently accurate for spectral deconvolution. The procedure for these experiments was the same as that for mixing Ngb-H64Q with pure HbCO in the Cary 50, after preparation of carboxylated red cells.

Least Squares Deconvolution

Standard reference spectra of the oxidized (met), deoxygenated (deoxy), oxygenated ($O_2$) and carboxylated (CO) forms of hemoglobin (Hb) and neuroglobin H64Q (Ngb-H64Q) were obtained. After thawing protein on ice, spectra of the oxidized form were obtained by mixing with an excess of potassium ferricyanide and passing through an ECONO-PAC™ 10DG Desalting Column (Bio-Rad Laboratories, Hercules, CA). Spectra of deoxygenated species were recorded after adding an excess of sodium dithionite to the oxidized form. Spectra of the oxygenated form were recorded immediately after passing deoxygenated species through the desalting column under aerobic conditions. Spectra of the carboxylated form were measured after mixing the deoxygenated species with CO-saturated buffer in a ratio of 1:4. All standard spectra were collected at 20° C., 25° C., and 37° C. on the Cary 50 spectrophotometer.

Deconvolution of experimental spectra was performed with a least-squares fitting routine in Microsoft Excel. Because the change in absorbance of the kinetic experiments is not great, all spectra composed of both Hb and Ngb-H64Q were always fit between 450 and 700 nm, 490 and 650 nm, and 510 and 600 nm, with and without constraining the Hb and Ngb-H64Q concentrations to be equal to each other, in order to confirm the accuracy of the deconvolution. Absorbance spectra from anaerobic experiments were deconvoluted using carboxylated and deoxygenated standards of Hb and Ngb-H64Q. Absorbance spectra from aerobic experiments were deconvoluted using the standards of the oxidized, carboxylated and oxygenated forms of Hb and Ngb-H64Q. For the red cell experiments where Hb was separated from Ngb-H64Q and dithionite was afterwards added to either red cells in aerobic experiments or to the supernatant in anaerobic experiments, deoxygenated standards were used in deconvolution instead of the oxygenated and oxidized forms. Before deconvoluting spectra collected with the Stopped-Flow spectrometer, and sometimes those with the HP8453, absorbance values were remapped to the same wavelengths as those used by the Cary 50 spectrophotometer using the interp1 function of MATLAB™, employing piecewise cubic hermite interpolation.

Results

The reaction of carboxylated red blood cells (RBCs) with either buffer or a solution of deoxy H64Q neuroglobin was studied (FIG. 1). When the RBCs were mixed with buffer, no appreciable change in the ratio of HbCO occurred (FIG. 1, left panel). When the cells were mixed with the deoxyNgb mutant, all CO was removed from the RBCs within about 15 minutes. The changes in the neuroglobin fraction are consistent with a transfer of CO from Hb to Ngb.

Another experiment with similar conditions is shown in FIG. 2. The reaction was completed in just over 10 minutes, consistent with the previous results shown in FIG. 1.

Figure 3:
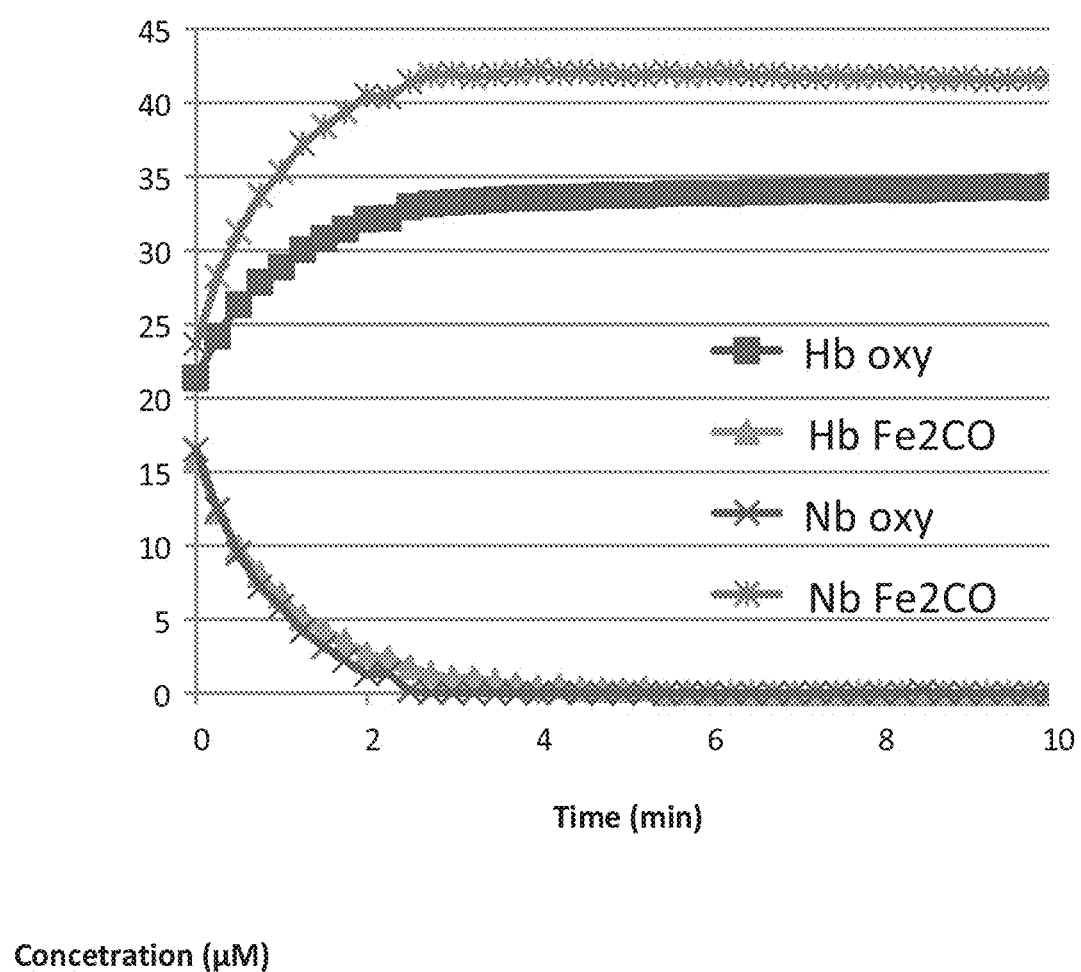
FIG. 3 is a graph showing the reaction of carboxylated red blood cells with oxyNgb H64Q. The experiment was performed at 21° C. in PBS buffer in aerobic conditions. Shown are deoxy or carboxylated species for the RBC fraction: oxyHb (squares); HbCO (triangles); oxyNgb (X); NgbCO (asterisks).

In addition, the reaction of carboxylated red blood cells with oxy H64Q neuroglobin was evaluated (FIG. 3). As observed for the deoxyNgb, the oxygenated form is also able to scavenge CO from the red blood cells at an even faster rate than that observed in the previous experiment. The process is completed in less than 5 minutes. The changes in the neuroglobin fraction are consistent with a transfer of CO from Hb to Ngb.

Altogether, these results indicate that neuroglobin is able to remove CO from carboxylated hemoglobin that is located inside red blood cells (across compartment) within 5-10 minutes, a time scale suitable for clinical treatment.

Example 2

Auto-Oxidation Rates for WT and Mutant Neuroglobins

Ferrous-dioxygen complexes in heme proteins have intrinsic rates of auto-oxidation, where the oxygen molecule can take an electron from the heme iron to form oxidized heme and superoxide radical:

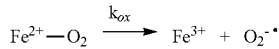

Auto-oxidation is a side reaction that can be detrimental for the intended neuroglobin applications (e.g., binding and removing CO from hemoglobin). For the purpose of treating carboxyhemoglobinemia, neuroglobin is infused as a ferrous dioxygen complex (oxy form, $Fe^{2+}$-$O_2$) that is able to: i) bind CO and ii) deliver oxygen to the tissues. Oxidation of the oxyneuroglobin leads to formation of the ferric form (met form, $Fe^{3+}$) that cannot accomplish either of the two functions mentioned above. The reaction also forms the radical superoxide species ($O_2^{-\bullet}$) that would cause increased oxidative stress.

The auto-oxidation rates for wild-type and several neuroglobin His64 mutants were determined and are summarized in Table 2.

TABLE 2

Auto-oxidation rates for wild-type neuroglobin and mutants

| | $K_{ox}$ (min$^{-1}$) | $t_{1/2}$ (min) |
|---|---|---|
| Human Neuroglobin, wild-type | 0.230 ± 0.030 | 3.0 |
| Human Neuroglobin, H64W | 0.076 ± 0.006 | 9.1 |
| Human Neuroglobin, H64A | 0.066 ± 0.005 | 10.5 |
| Human Neuroglobin, H64L | 0.010 ± 0.004 | 69.3 |
| Human Neuroglobin, H64Q | 0.010 ± 0.002 | 69.3 |

Values determined at 37° C. in sodium phosphate 100 mM, pH 7.4.
$t_{1/2}$; calculated half-life of the ferrous dioxygen complex.

Wild-type neuroglobin has a fast auto-oxidation rate; half of any existing ferrous-dioxygen complex is oxidized every 3 minutes. However, the neuroglobin mutants H64L and H64Q have auto-oxidation rates 23-fold slower than the wild type protein. Based on these findings, the H64Q mutant was selected for the in vivo studies described in Example 3.

Example 3

Recombinant H64Q Neuroglobin is an Antidote for Carboxyhemoglobinemia In Vivo

This example demonstrates that administration of a recombinant globin molecule that binds carbon monoxide with high affinity efficiently clears HbCO from the blood of CO-exposed mice and thus represents an antidote for carboxyhemoglobinemia and/or carbon monoxide poisoning. In the experiments described below, the CO is removed from red blood cells after a five minute infusion of recombinant mutant neuroglobin H64Q. The H64Q mutant neuroglobin used in the studies below also contains mutations at three cysteine residues (C46G/C55S/C120S).

In the following experiments, H64Q neuroglobin was administered at a dose ranging between 13.6 and 27.2 mg (4-8 mM). Blood volume in humans is approximately 5000× greater, therefore this dose range is equivalent to a human dose range of 68-136 grams.

Figure 4:
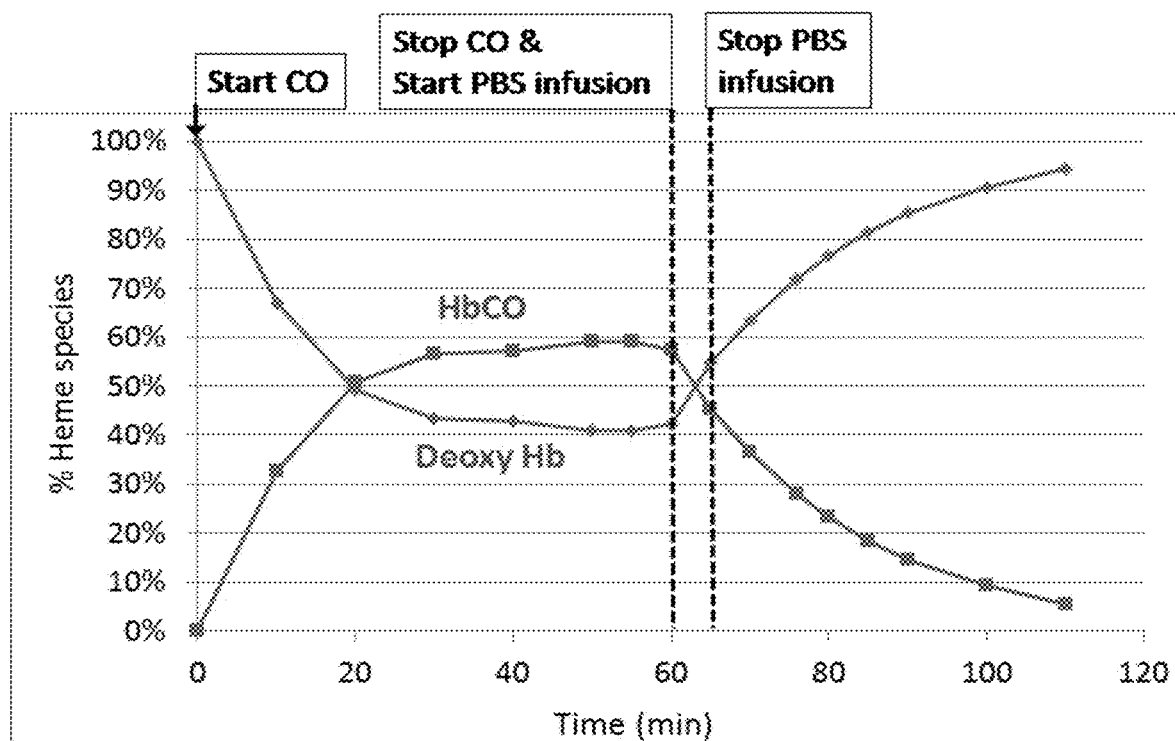
FIG. 4 is a graph showing the concentration of HbCO in the blood of CO-exposed mice. Mice were exposed to 1500 ppm CO for 60 minutes, then CO was stopped and PBS (200 μl) was infused for 5 minutes. Blood samples (approximately 10 μl) were drawn every 5-10 minutes, chemically reduced with dithionite and monitored for HbCO. Other Hb species in blood (oxyHb/metHb/deoxyHb) are represented as deoxy Hb.
Figure 5:
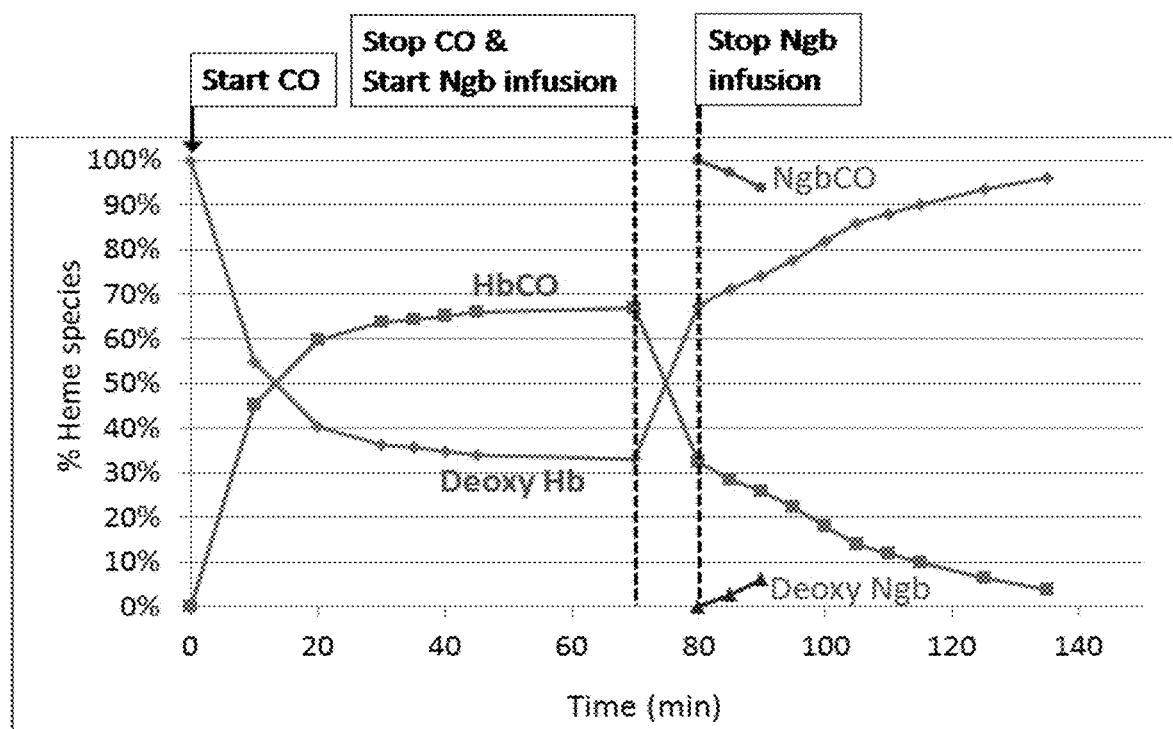
FIG. 5 is a graph showing the concentration of HbCO in the blood of CO-exposed mice. Mice were exposed to 1500 ppm CO for 70 minutes, after which CO was stopped and concentrated H64Q Ngb (200 μl) was infused for 10 minutes. Blood samples (about 10 μl) were drawn every 5-10 minutes, chemically reduced with dithionite and monitored for HbCO and NgbCO. Other Hb species in the blood (oxyHb/metHb/deoxyHb) are represented as deoxy Hb, and Ngb species (oxyNgb/metNgb/deoxyNgb) are represented as deoxy Ngb.
Figure 6:
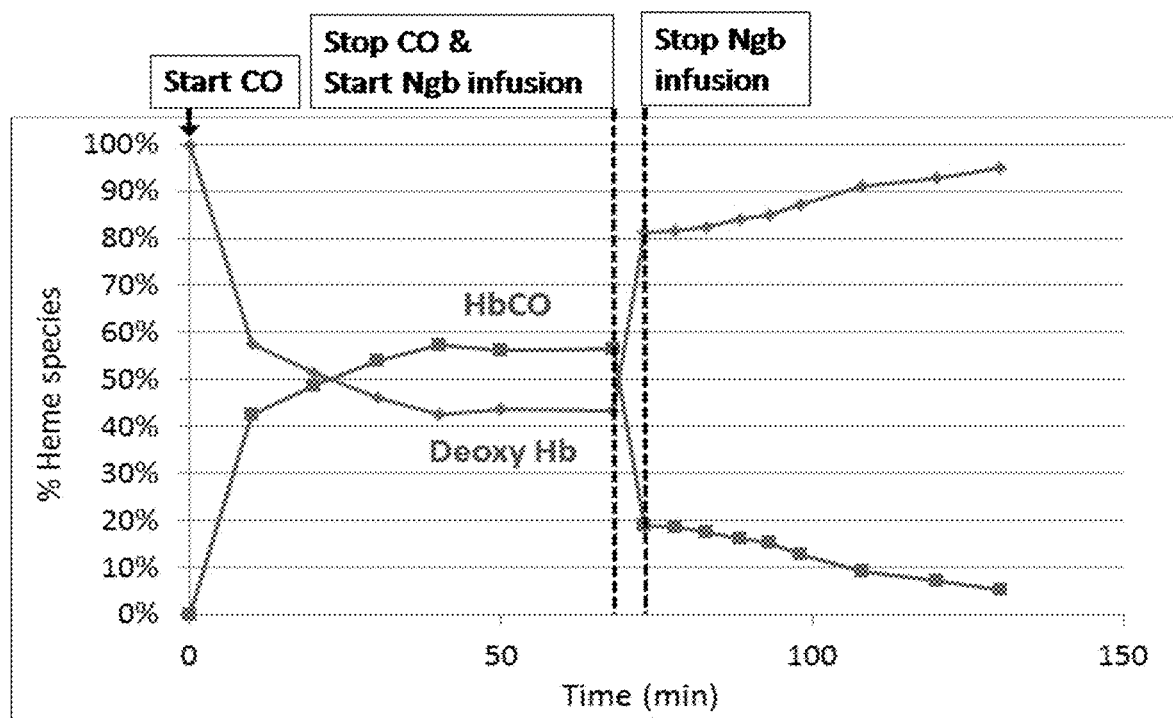
FIG. 6 is a graph showing the concentration of HbCO in the blood of CO-exposed mice. Mice were exposed to 1500 ppm CO for 70 minutes, after which CO was stopped and concentrated H64Q Ngb (200 μl) was infused for 5 minutes. Blood samples (approximately 10 μl) were drawn every 5-10 or 20 minutes, chemically reduced with dithionite and monitored for HbCO and NgbCO. Other Hb species in the blood (oxyHb/metHb/deoxyHb) are represented as deoxy Hb.

The capacity of recombinant H64Q neuroglobin to remove HbCO from blood in vivo was evaluated in CO-exposed mice. Mice were exposed to 1500 ppm CO for 60-70 minutes, CO was then stopped and either PBS (200 µl) or concentrated H64Q neuroglobin (200 µl) was infused for 5 minutes (PBS—FIG. 4; H64Q neuroglobin—FIG. 6) or 10 minutes (H64Q neuroglobin—FIG. 5). Blood samples (approximately 10 µl) were drawn every 5-10 minutes, the red cells were washed, lysed and chemically reduced with dithionite and monitored for HbCO and NgbCO. This assay shows the amount of CO that is in the red blood cell before and after the H64Q NgB infusion in vivo. As shown in FIGS. 5 and 6, infusion of H64Q neuroglobin rapidly removes HbCO from the blood within the 5 or 10 minute infusion period.

Figure 7A:
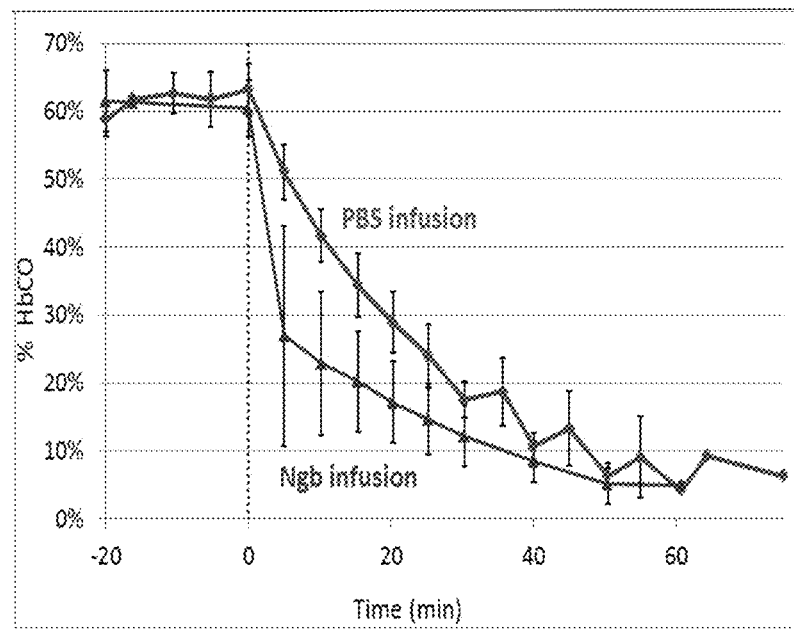
FIGS. 7A-7B are a pair of graphs showing decay of the concentration of HbCO in the blood of CO-exposed mice after PBS or H64Q neuroglobin infusion.
Figure 7B:
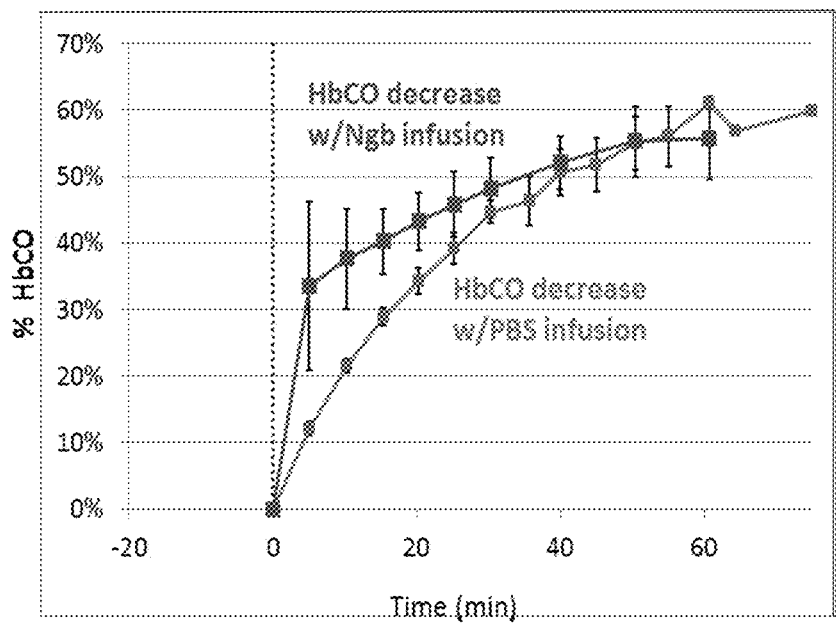
Figure 8:
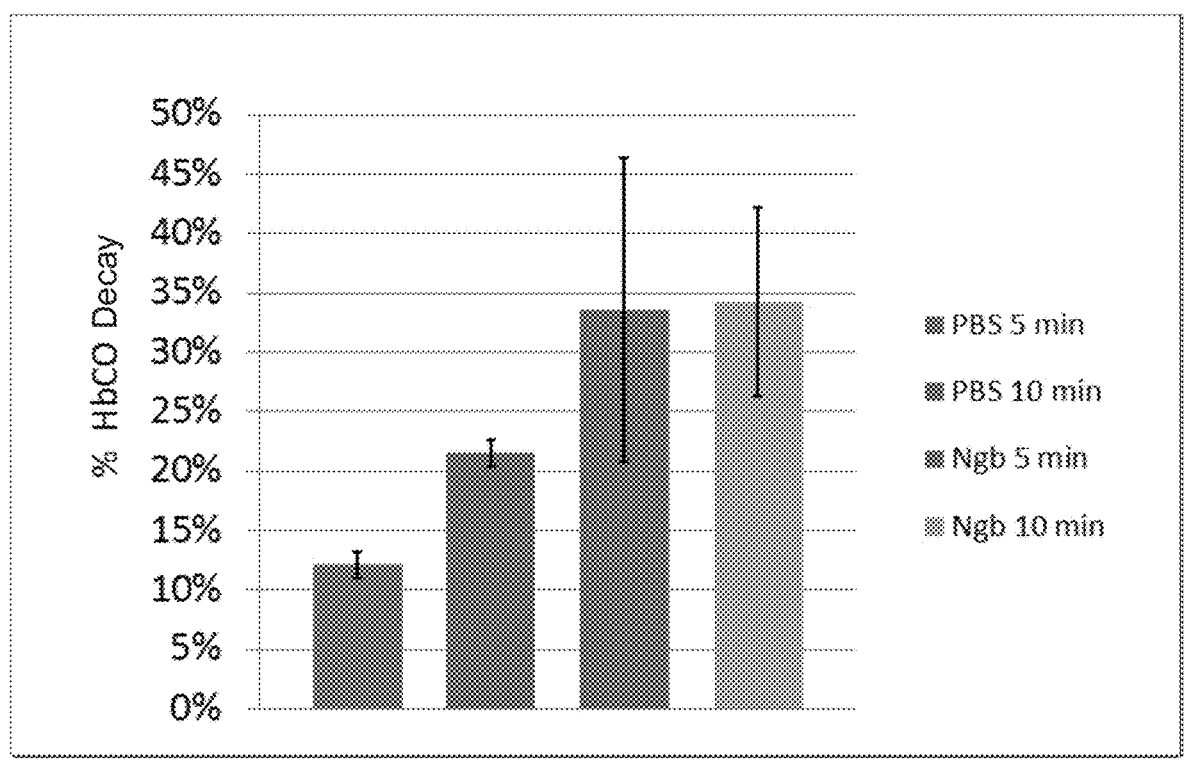
FIG. 8 is a graph showing percent decay of the concentration of HbCO in the blood of CO-exposed mice 5 and 10 minutes after PBS or H64Q neuroglobin infusion. Bars represent from left to right: PBS infusion for 5 minutes; PBS infusion for 10 minutes; H64Q Ngb infusion for 5 minutes; and H64Q Ngb infusion for 10 minutes.

The decay in concentration of HbCO in the blood of CO-exposed mice after a five-minute infusion of PBS or H64Q neuroglobin is shown in FIGS. 7A and 7B. FIG. 7A shows absolute HbCO levels over time and FIG. 7B shows the relative change in HbCO level over time. The results shown in these figures clearly demonstrate that infusion of H64Q neuroglobin leads to a more rapid clearance of HbCO from the blood, and a greater relative change in HbCO over time, than infusion with PBS. Similarly, FIG. 8 shows that infusion of H64Q for either 5 or 10 minutes leads to a greater percent HbCO decay compared with infusion of PBS for the same period of time.

Figure 9A:
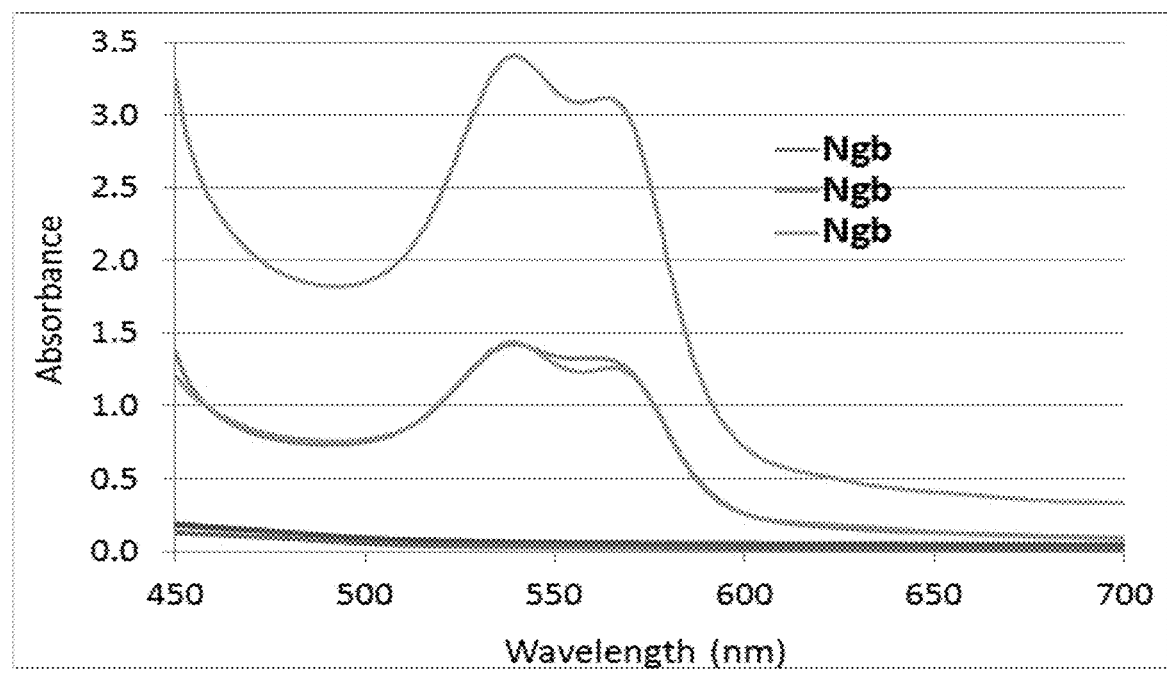
FIG. 9A is a graph demonstrating that H64Q neuroglobin is cleared as NgbCO in the urine of infused mice. Shown is the absorbance of urine from bladders of mice sacrificed approximately 75 minutes after the end of CO exposure. The top three traces show the absorbance due to neuroglobin, which include 82 to 91% NgbCO. The bottom traces indicate the absorbance that is not attributable to Ngb.
Figure 9B:
FIG. 9B is a photograph of the internal organs of an H64Q Ngb-treated mouse and a syringe with red-colored urine containing NgbCO.

To confirm that neuroglobin is cleared as NgbCO in the urine of infused mice, absorbance of urine from bladders of mice sacrificed approximately 75 minutes after the end of CO exposure was determined. The results are shown in FIG. 9A. The top three traces show the absorbance due to neuroglobin, which include 82 to 91% NgbCO. The bottom traces indicate the absorbance that is not attributable to Ngb. In addition, the presence of NgbCO in the urine of CO-exposed mice was confirmed by the presence of red-colored urine in these mice (see syringe in FIG. 9B).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of treating carboxyhemoglobinemia in a subject, comprising:
    selecting a subject with carboxyhemoglobinemia; and
    administering to the subject a therapeutically effective amount of a recombinant globin molecule that binds carbon monoxide with high affinity, wherein the recombinant globin molecule comprises:
        a human recombinant neuroglobin with a H64Q, H64L, H64A or H64W mutation, and further comprising a C46G mutation, a C55S mutation and a C120S mutation; or
        a human recombinant cytoglobin with a H81Q, H81A, H81L or H81W mutation, and further comprising a C38S mutation and a C83S mutation,
    thereby treating carboxyhemoglobinemia in the subject.

2. The method of claim 1, wherein the human recombinant neuroglobin comprises the amino acid sequence of SEQ ID NO: 3.

3. The method of claim 1, wherein the human recombinant cytoglobin comprises the amino acid sequence of SEQ ID NO: 6.

4. The method of claim 1, wherein the subject has at least 3% carboxyhemoglobin in their blood.

5. The method of claim 1, wherein the recombinant globin molecule is administered by intravenous infusion.

6. A method of removing carbon monoxide from hemoglobin in blood or tissue, comprising contacting the blood or tissue with a recombinant globin molecule that binds carbon monoxide with high affinity, wherein the recombinant globin molecule comprises:
    a human recombinant neuroglobin with an H64Q, H64L, H64A or H64W mutation, and further comprising a C46G mutation, a C55S mutation and a C120S mutation; or
    a human recombinant cytoglobin with an H81Q, H81A, H81L or H81W mutation, and further comprising a C38S mutation and a C83S mutation,
    thereby removing carbon monoxide from hemoglobin in the blood or tissue.

7. The method of claim 6, wherein the human recombinant neuroglobin comprises the amino acid sequence of SEQ ID NO: 3.

8. The method of claim 6, wherein the human recombinant cytoglobin comprises the amino acid sequence of SEQ ID NO: 6.

9. The method of claim 6, which is an in vitro method.

10. The method of claim 6, which is an in vivo method, wherein contacting the blood or tissue with a recombinant globin molecule comprises administering the recombinant globin molecule to a subject.

11. The method of claim 10, wherein the subject has at least 5% carboxyhemoglobin in their blood.

12. The method of claim 10, wherein the recombinant globin molecule is administered by intravenous infusion.

13. A human recombinant globin molecule comprising:
    a human recombinant neuroglobin comprising a mutation at residue 64, and further comprising a C46G mutation, a C55S mutation and a C120S mutation; or
    a human recombinant cytoglobin comprising a mutation at residue 81, and further comprising a C38S mutation and a C83S mutation.

14. The human recombinant globin molecule of claim 13, wherein the mutation at residue 64 of the human recombinant neuroglobin is a H64Q, H64L, H64A or H64W mutation; or wherein the mutation at residue 81 of the human recombinant cytoglobin is a H81Q, H81A, H81L or H81W mutation.

15. The human recombinant globin molecule of claim 14, comprising the amino acid sequence of SEQ ID NO: 3 or SEQ ID NO: 6.

16. A composition comprising the human recombinant globin molecule of claim 13 and a pharmaceutically acceptable carrier.

17. The human recombinant globin molecule of claim 14, wherein the human recombinant globin molecule is in monomeric form.

18. The composition of claim 16, wherein the pharmaceutically acceptable carrier is selected from the group consisting of a wetting agent, an emulsifying agent, a preservative, and a pH buffering agent.

19. The composition of claim 16, wherein the pharmaceutically acceptable carrier is selected from the group consisting of sodium acetate and sorbitan monolaurate.

20. The composition of claim 16, wherein the human recombinant globin molecule is present in a therapeutically effective amount.

* * * * *